United States Patent [19]
Goldhaber et al.

[11] 4,251,310
[45] Feb. 17, 1981

[54] METHOD FOR REBONDING TUBING ELEMENTS USED IN NEEDLE ASSEMBLIES

[75] Inventors: Richard P. Goldhaber; John M. Munsch, both of Libertyville; Ludwig Wolf, Jr., Crystal Lake, all of Ill.

[73] Assignee: Baxter Travenol Laboratories, Inc., Deerfield, Ill.

[21] Appl. No.: 854,762

[22] Filed: Nov. 25, 1977

[51] Int. Cl.³ .................... B29C 19/04; B29C 19/06; A61M 5/00
[52] U.S. Cl. .................................. 156/273; 156/275; 156/308.2; 156/272; 156/294; 128/218 N
[58] Field of Search ............... 156/272, 273, 275, 308, 156/294; 128/218 N

[56] References Cited
U.S. PATENT DOCUMENTS
3,174,890  3/1965  Goyke .................. 156/272

FOREIGN PATENT DOCUMENTS
1130615  10/1968  United Kingdom ..................... 156/273

OTHER PUBLICATIONS
*Hackh's Chemical Dictionary*, Fourth Edition, McGraw Hill Book Company, N.Y., 1969, p. 712.

Primary Examiner—John T. Goolkasian
Assistant Examiner—Lois E. Rodgers
Attorney, Agent, or Firm—Paul C. Flattery; Gerald S. Geren

[57] ABSTRACT

There is disclosed herein an improved needle assembly or fistula set which includes a hollow metal needle, a larger plastic fluid-carrying conduit, and plastic spacers between the needle and the conduit. The conduit and spacers are heat sealed to each other so as to provide a fluid-tight junction with the needle.

A method for heat sealing the fistula set is also disclosed. In that method, the needle is used as one electrode and the other electrode includes jaw-like members which engage and surround the conduit at the junction where the heat seal is to be formed. During the heat sealing operation, the conduit and needle are maintained in substantial coaxial alignment so as to assure coaxial alignment thereafter.

A fixture or tooling apparatus is also disclosed for effecting heat sealing and assuring substantial coaxial alignment.

4 Claims, 3 Drawing Figures

METHOD FOR REBONDING TUBING ELEMENTS USED IN NEEDLE ASSEMBLIES

BACKGROUND OF THE INVENTION

This invention relates to a medical apparatus, and more particularly, to a needle assembly for conducting biological fluids to and from a patient.

In medically treating a patient, it is sometimes necessary (1) to introduce fluids, such as intravenous solutions, blood, etc., into the patient's body, or (2) to remove fluids from the patient. This may be accomplished by employing a needle assembly which is sometimes referred to as a fistula set. Such assemblies include a hollow metal needle for insertion into a vein or artery and an appropriate conduit connected to the other end of the needle through which the fluid can flow to or from the patient.

The needle is made from small diameter hollow stainless steel tubing, one end of which has been ground to provide a beveled edge for insertion into a vein or artery. The conduit is normally a larger tube made of medical grade polyvinylchloride which has an inside diameter substantially larger than the outside diameter of the steel tubing.

The conduit must be sealed to the needle so as to avoid any leakage of fluid at that junction. One method for sealing such needle assemblies has been to employ spacer members which are solvent sealed to each other and to the conduit using cyclohexanone. In one particular assembly, a thin layer of adhesive is bonded to the periphery of the needle at the butt end (i.e., the end opposite the beveled end) and then a vinyl sleeve is shrink-fitted about the adhesive. The adhesive bonds to the steel tube and provides a roughened surface for establishing a mechanical bond between the sleeve and the adhesive. A spacer or collar is then fitted about the sleeve. The collar has an outside diameter normally sufficient to engage the inside diameter of the conduit. The sleeve, collar and conduit have been solvent sealed to one another so as to provide a leak-free junction.

It has been found to be desirable to provide a more reliable junction between the needle and conduit than has been available by solvent sealing, but without changing the physical structure of the fistula set.

In addition to solvent sealing, there exists other sealing techniques, such as mechanical or radio frequency (RF) heat sealing. Mechanical sealing would require application of a binding member about the outside diameter of the conduit so as to mechanically hold the conduit, spacer, sleeve and needle together and was felt to be undesirable from a manufacturing point of view. RF heat sealing of plastic conduits is known and normally requires the use of (1) a removable solid brass or other highly electrically conductive metal mandrel as one electrode which is inserted into the conduit and (2) an external electrode applied around the outside of the conduit. Due to the small inside diameter of the needle, it was known that such a mandrel would be difficult to insert for heat sealing purposes. Furthermore, due to the hollow shape of the needle and that it was made of stainless steel rather than brass, it was not believed that RF heat sealing of the junction could be effected reliably in an isolated location using the needle as a mandrel.

It is therefore another object of this invention to provide an appropriate method for sealing the needle assembly.

These and other objects of the invention will become apparent from the following description and appended claims.

SUMMARY OF THE INVENTION

It has been discovered that an improved needle assembly or fistula set can be provided whereby the conduit is RF heat sealed to the spacers so as to provde a fluid-tight junction with the needle. Quite unexpectedly, it was discovered that the hollow stainless steel needle itself, which remains as part of the fistula set, can be used as one of the electrodes in the RF sealing process.

Furthermore, a new apparatus has been provided for use in the heat sealing operation which, among other things, assures coaxial alignment of the needle and the conduit during and after heat sealing and makes electrical contact with the needle.

DESCRIPTION OF THE PREFERRED EMBODIMENT

Figure 1:
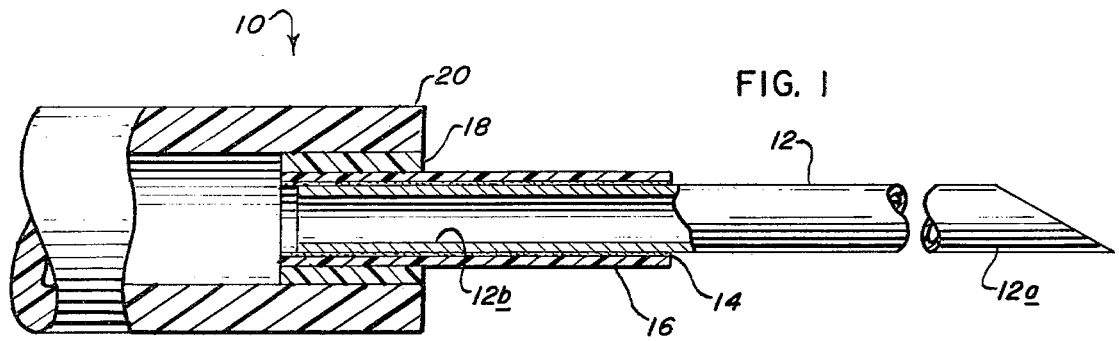
FIG. 1 is a sectional view taken along the longitudinal axis of the fistula set showing the various elements of the fistula set prior to heat sealing.

Referring now to FIG. 1, the fistula set or needle assembly 10 is shown. The fistula set includes a hollow, small diameter stainless steel needle 12 which has a beveled end 12a for insertion and a butt end 12b. A very thin adhesive layer 14 is applied about the butt end of the needle and bonds thereto. A vinyl sleeve 16 is shrink fitted over the adhesive layer 14 and mechanically bonds to the adhesive. A shorter spacer or collar 18 is fitted about the sleeve 16 and has an inner diameter which permits engagement with the shrink-fitted sleeve 16. A vinyl conduit or tube 20 fits over the collar 18 and completes the junction between the needle 12 and conduit 20. The inside diameter of the tube 20 and outside diameter of the collar 18 are selected so as to provide engagement therebetween. To facilitate production and enhance reliability, cyclohexanone may be used to lubricate the sleeve, collar and conduit for ease of assembly and to seal the members to each other.

Figure 2:
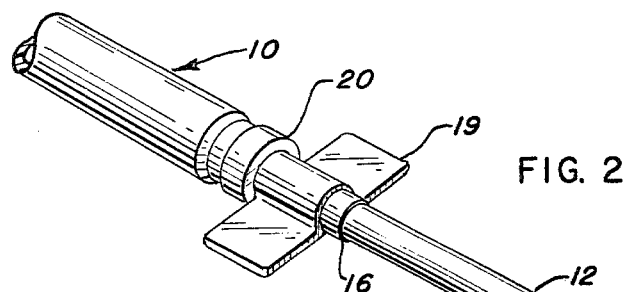
FIG. 2 is a perspective view of the fistula set showing the exterior of the junction after heat sealing.

The tubing 20, collar 18 and sleeve 16 are heat sealed to each other. During heat sealing, the adhesive 14 may be activated so as to provide a physical/chemical bond between the needle 12 and shrink-fit sleeve 16. Furthermore, the tube 20, collar 18 and sleeve 16 fuse together so as to assure a leak-free junction between the needle 12 and tube 10. As can be seen in FIG. 2, a depression is formed about the junction where the heat sealing has been effected. A "butterfly" needle positioner 19 is fitted about the needle on the shrink-fit sleeve 16 and adjacent the conduit 20.

Figure 3:
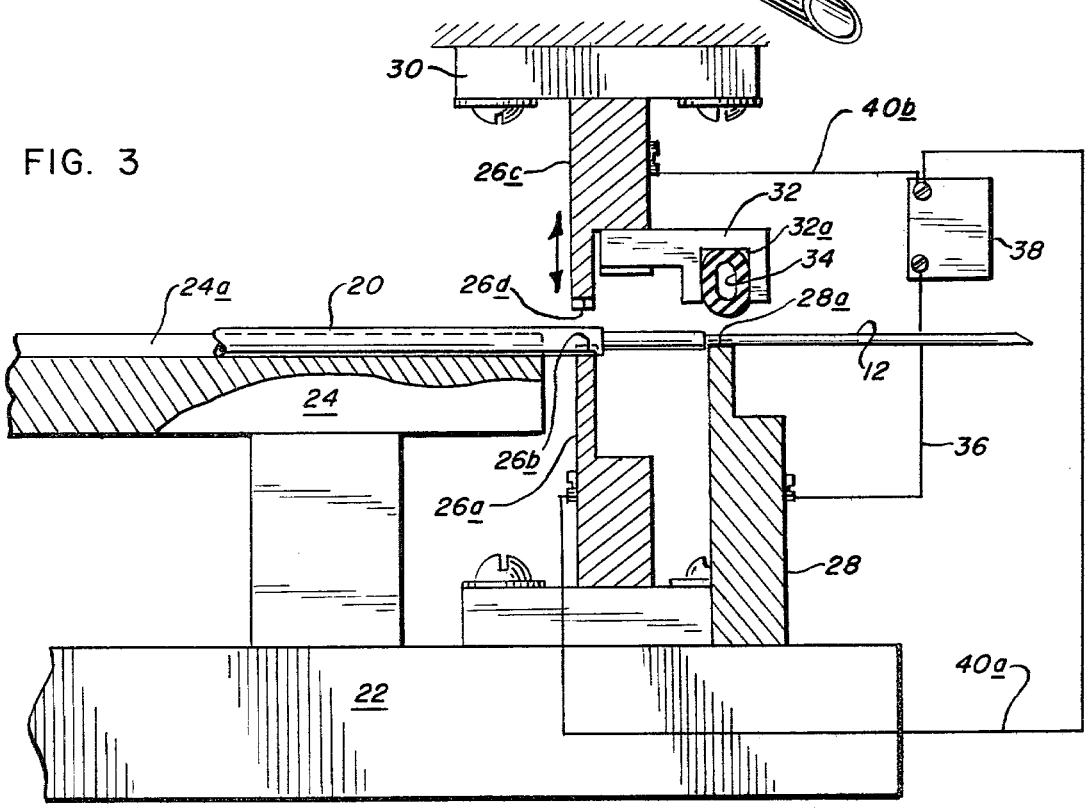
FIG. 3 is an elevational view showing the improved tooling for heat sealing the fistula set.

Referring now to FIG. 3, the tooling for heat sealing is shown. The tooling includes a dielectric base 22 on which is mounted an elongated conduit support 24. The support has an inner groove 24a within which the conduit 20 rests. One-half of a heat-sealing jaw-type electrode 26a is mounted to the base 22 and is positioned in spaced relationship to the conduit support 24. The electrode 26a also includes a groove-like portion 26b for receiving and engaging the portion of the conduit 20 which overlies the butt end 12b of the needle 12. Another heat sealing electrode 28 is also mounted to the base 22, is positioned so as to engage the needle 12, and has a V-groove 28a for receiving the needle. This electrode 28 cooperates in locating the needle 12 coaxially with the axis of the conduit 20. The heat sealing electrode 28 can be adjustably positioned so as to accommodate needles of different diameters.

The tooling also includes a downwardly movable head 30 which carries the other half of the jaw-like electrode 26c, which as a conduit-engaging groove 26d. The jaws 26a and 26c are aligned and are constructed to engage and squeeze the conduit 20.

A needle-engaging and position-maintaining bracket 32 is carried by the head 30 and the electrode 26c. The bracket 32 is fabricated from an insulating material and includes a recess 32a having a flexible needle -engaging member 34. The support 24, the electrode 26a, and the electrode 28 are all arranged so as to assure substantial coaxial alignment between the needle 12 and conduit 20 during and after heat sealing.

The needle-engaging electrode 28 is connected via line 36 to a RF heat sealing machine 38. Such machines are commercially available and may be purchased from suppliers, such as J. A. Callanan Company of Chicago, Ill. The jaw electrodes 26a and 26c are commonly connected via lines 40a and 40b to the RF sealing machine 38. The jaw electrodes 26a and 26c and the needle-engaging electrode 28 can be used interchangeably as the cathode or anode. However, it is preferable that the needle-engaging electrode 28 be the anode.

In operation, the head 30 is initially in an upward position, and an assembled but not heat-sealed fistula set 10, is positioned so that the conduit rests and is immobilized on the support 24, the needle 12 rests on the electrode 28 and the junction with the spacer collar 18 is positioned between the jaws 26a and 26c. The head 30 is then moved downwardly so as to grasp and apply pressure to the conduit 20 at the junction, assure engagement and alignment between the needle 12 and electrode 28, and secure the needle 12 to the electrode 28. A RF current is then passed through the electrode 28, needle 12, through the junction and to the jaws 26a and 26c. This RF current fuses the conduit 20, spacer collar 18 and the shrink-fit sleeve 16 to one another and activates the adhesive 14 so as to provide the aggressive bond. Thereafter, current flow is terminated, the head 30 is retracted and the heat-sealed needle assembly is removed from the tooling with the conduit 20 and needle 12 in axial alignment.

It will be appreciated that numerous changes and modifications can be made in the embodiment disclosed herein without departing from the spirit and scope of this invention.

What is claimed is:

1. A method for manufacturing a needle assembly having a fluid-tight seal, which assembly includes a hollow metal needle, a plastic conduit for carrying biological fluids, plastic sleeve means and plastic spacer means between said needle and said conduit, and adhesive means between said needle and sleeve means, wherein the improvement comprises the steps of employing said needle as one electrode applying a second electrode about the conduit and passing an RF heat-sealing electric current between the needle and electrode so as to fuse said conduit, said spacer means and said sleeve means and provide a fluid-tight junction between the conduit and needle.

2. A method as in claim 1, wherein said needle is used as the anode and the electrode positioned above the conduit is used as the cathode.

3. A method as in claim 1, wherein said needle and said conduit are maintained in substantial coaxial relation during manufacture.

4. A method as in claim 1, wherein prior to heat sealing and during initial assembly, a solvent is applied to said conduit and said spacer means.

* * * * *